United States Patent [19]

Knute et al.

[11] Patent Number: 4,903,707

[45] Date of Patent: Feb. 27, 1990

[54] VENTRICULAR CATHETER ASSEMBLY

[75] Inventors: Wallace L. Knute, Leucadia; Stephens Sato, Del Mar, both of Calif.

[73] Assignee: Camino Laboratories, San Diego, Calif.

[21] Appl. No.: 185,173

[22] Filed: Apr. 22, 1988

[51] Int. Cl.$^4$ .............................................. A61B 5/00
[52] U.S. Cl. ................................... 128/748; 604/175
[58] Field of Search ............ 128/748, 303 B, DIG. 6; 604/175, 8, 9

[56] References Cited

U.S. PATENT DOCUMENTS

| | | | |
|---|---|---|---|
| 3,669,094 | 6/1972 | Heyer | 128/748 |
| 4,186,728 | 2/1980 | van Lotringen | 128/748 X |
| 4,354,506 | 10/1982 | Sakaguchi et al. | 128/748 |
| 4,572,212 | 2/1986 | Letterio | 128/748 |
| 4,629,451 | 12/1986 | Winters et al. | 128/303 R X |
| 4,646,752 | 3/1987 | Swann et al. | 128/748 |
| 4,676,782 | 6/1987 | Yamamoto et al. | 604/175 |
| 4,677,985 | 7/1987 | Bro et al. | 128/748 X |

Primary Examiner—Max Hindenburg
Assistant Examiner—J. P. Lacyk
Attorney, Agent, or Firm—Fulwider, Patton Reiber, Lee & Utecht

[57] ABSTRACT

A catheter assembly comprising a catheter having a lumen and characterized by a flexible distal extremity. The assembly further comprises a bolt having a threaded distal extremity for threading into an opening in the skull in sterile relation. The bolt includes an elongated chamber extending between its distal extremity and a threaded proximal extremity of the bolt. The catheter is disposed through the bolt chamber, and includes an opening from the lumen to the exterior of its flexible distal extremity. A clamp is threaded onto the catheter proximal extremity and is operative to forcibly engage the catheter and constrain it against movement relative to the bolt to thereby maintain a predetermined depth of insertion of the catheter into the skull.

12 Claims, 2 Drawing Sheets

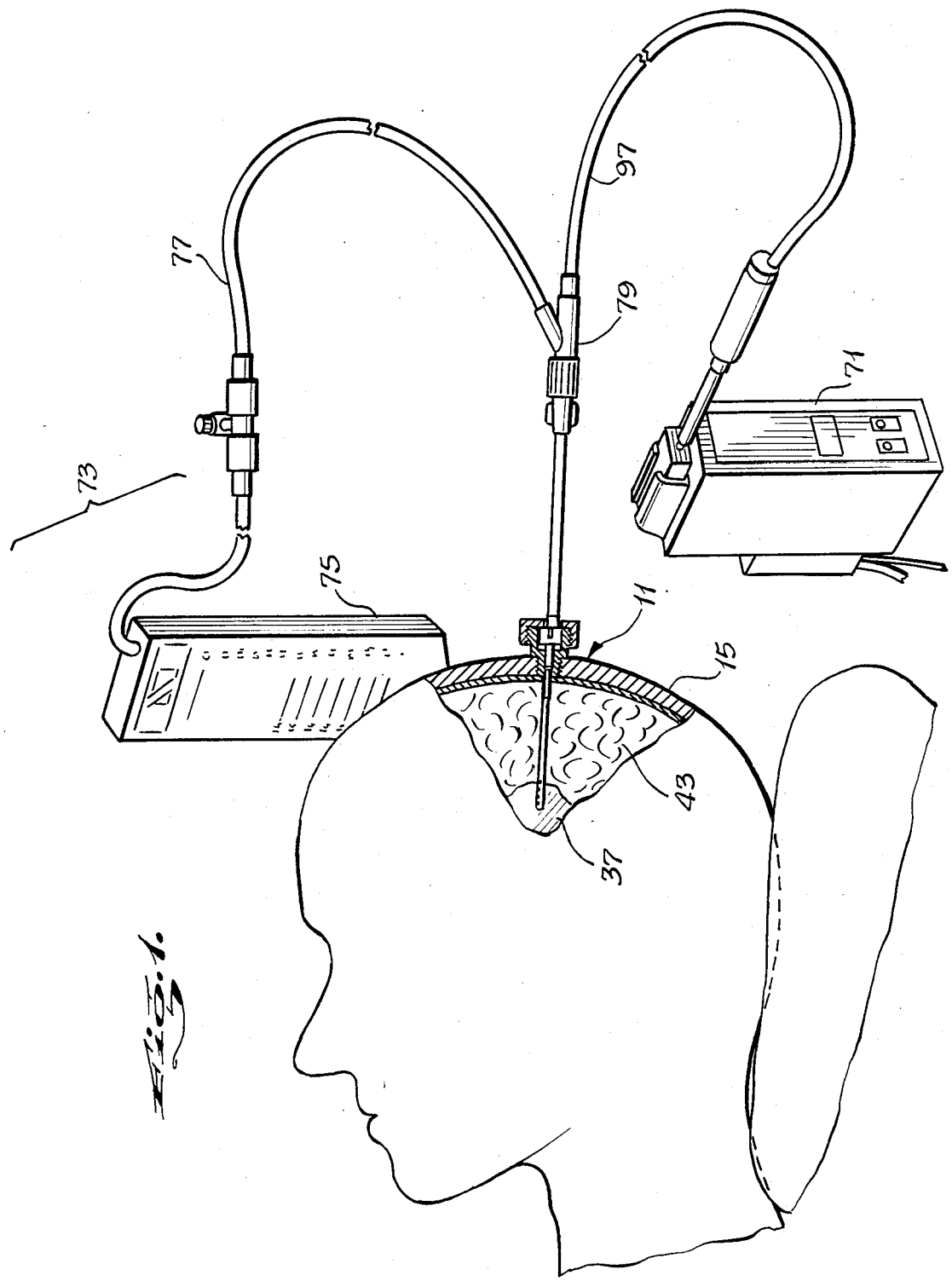

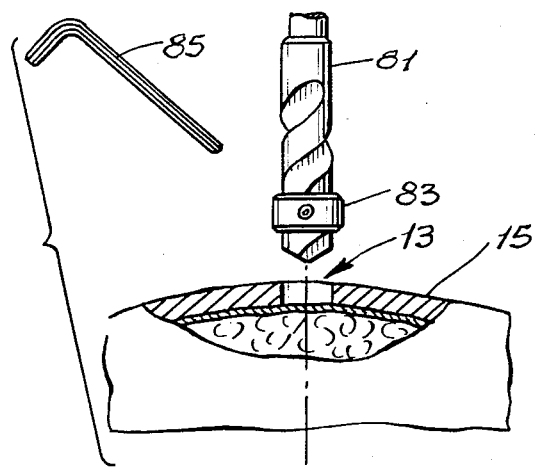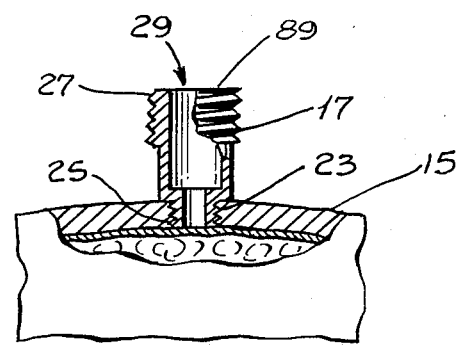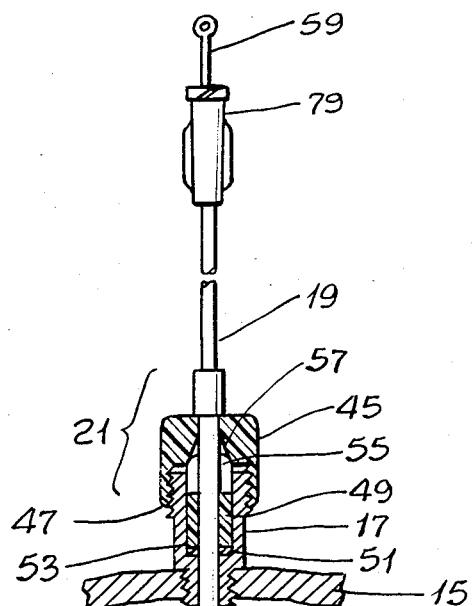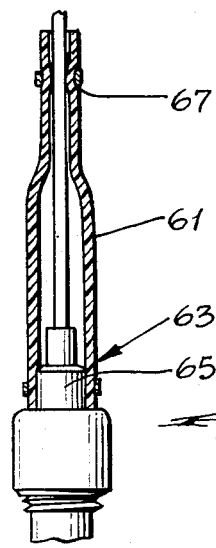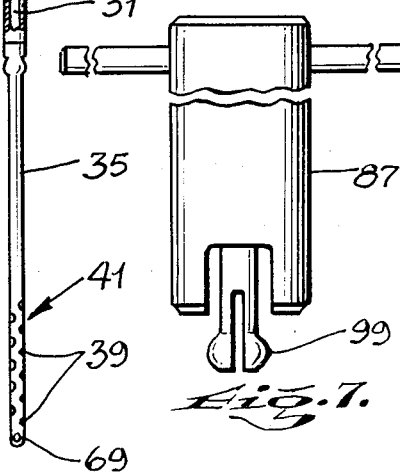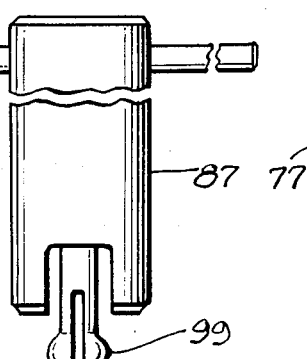

4,903,707

VENTRICULAR CATHETER ASSEMBLY

BACKGROUND OF THE INVENTION

The present invention relates generally to a catheter assembly having a catheter for insertion through an opening in a skull for monitoring a parameter of a brain of a living patient.

In the event of certain medical occurrences such as trauma to the head it is necessary to monitor the pressure in a ventricle of the brain and if the pressure rises above a critical level to relieve the pressure by draining fluid from the ventricle. A catheter or the like must be inserted directly into the brain to accomplish these tasks, but insertion of such a catheter has been a difficult and risky procedure. Among the risks of inserting a catheter into the brain is the risk of bacterial infection. As a general rule, once the catheter has been inserted it must be left in place for several days, and this makes the prevention of such infection both critically important and very difficult to accomplish.

It is possible to insert such a catheter surgically through an opening in the skull, routing the catheter underneath the scalp against the surface of the skull for a significant distance from the opening in the skull and thence through an opening in the scalp to the outside world. This isolates the opening in the skull from any contact with the environment outside the scalp and thereby minimizes the opportunity for infectious agents to enter the opening in the skull. However, insertion of the catheter by this method is time consuming, requires considerable surgical skill, and does not entirely eliminate the risk of infection.

Accordingly, there is a need for a fast and simple way to insert a catheter through the skull, through the brain, into the ventricle and to secure the catheter in position for as much as several days while avoiding any risk of infection.

SUMMARY OF THE INVENTION

The present invention provides a ventricular catheter assembly having a catheter which can be quickly and easily inserted through an opening in a skull of a living patient to monitor a parameter of the brain without creating a risk of infection. The catheter can be inserted without any need of extensive surgical procedure and once installed can remain in place for as long as required.

Briefly and in general terms, a ventricular catheter assembly according to the invention comprises blot means for insertion into an opening in the skull and having a an elongated chamber therethrough, a catheter having a rigid portion adapted to fit slidingly within the opening through the bolt means and a flexible portion adapted to penetrate into a ventricle of the brain, and clamping means for clamping the rigid portion of the catheter to the bolt means whereby the catheter can be inserted through the opening in the bolt means into the brain to a desired depth and then clamped to remain in a fixed position with reference to the brain.

A distal extremity of the bolt means is adapted for insertion into the opening in the skull in a sterile relation. In a preferred embodiment the distal extremity is tapered and includes male threads carried by the first distal extremity and operative to screw into the opening in the skull when the bolt means is twisted as with a wrench. The fluid-tight mounting provides isolation between the interior of the skull and the outside environment, thereby reducing the potential for infection.

The catheter defines a lumen and an opening from the lumen to an exterior surface of the flexible portion of the catheter provides for communication between the lumen and any brain tissue adjacent the catheter.

The clamping means is adapted for clamping to a proximal extremity of the bolt means and when clamped forcibly engages the catheter and constrains the catheter against movement relative to the mounting means.

Preferably a removable stylet is provided to fit within the catheter to stiffen the catheter during the process of inserting the catheter into the brain.

In one embodiment a sterility sleeve is provided to enclose the catheter outside the bolt means, the sleeve having a first extremity connected to the clamping means and a second extremity adapted to slidably engage the catheter, thereby enclosing the catheter between the first and second extremities in a sterile relation.

Pressure within the ventricle is preferably monitored by means of a transducer adapted for insertion into the catheter and operative to provide a signal indicative of ventricular fluid pressure within the brain adjacent the opening in the flexible portion of the catheter. A pressure monitor receives the signal and provides a readout of the pressure.

Preferably the catheter includes means for draining fluid from the ventricle. Such means includes, for example, a vessel to receive the fluid, a conduit to carry the fluid to the vessel, and a coupling to couple the conduit means to the catheter.

Optionally the catheter is provided with an installation kit which includes a drill for drilling an opening through the skull to receive the bolt means, a drill stop adapted for installation on the drill, means such as a small wrench for installing the drill stop at a desired location on the drill to fix a maximum depth to which the drill can penetrate, and means such as a socket wrench for tightening the bolt means into the opening in the skull.

Other aspects and advantages of the present invention will become apparent from the following detailed description, taken in conjunction with the accompanying drawings, illustrating by way of example the principles of the invention.

BRIEF DESCRIPTION OF THE DRAWINGS

FIG. 1 shows a preferred embodiment of the invention with the catheter located in a ventricle of a human brain;

FIG. 2 shows a drill for drilling a hole in the skull for insertion of the catheter shown in FIG. 1;

FIG. 3 shows the bolt means installed in the hole in the skull;

FIG. 4 shows a sectional view of the catheter;

FIG. 5 shows a sterile sleeve in position on the catheter;

FIG. 6 shows a coupling for connecting the catheter to a drain; and

FIG. 7 shows a wrench for installing the bolt means in the skull.

DESCRIPTION OF THE PREFERRED EMBODIMENT

As shown in the drawings for purposes of illustration, the invention is embodied in a novel ventricular catheter for monitoring a brain parameter of a living patient through an opening in the skull. Insertion of catheters into the brain has required much surgical skill and has carried a significant risk of infection, especially when it has been necessary for the catheter to remain in position for an extended period of time. A catheter according to the invention can be quickly and easily inserted and forms a sterile connection with the skull whereby the catheter can be left in place for as long as desired without the risk of infection.

Turning now to the drawings, a ventricular catheter designated generally 11 for monitoring a brain parameter through an opening 13 in a skull 15 of a living patient includes bolt means 17, a catheter 19 and clamping means 21. The bolt means 17 has a distal extremity 23 adapted for insertion into the opening 13 in the skull 15, said extremity 23 including means such as threads 25 for mounting the bolt means 17 the skull 15 in a fluid-tight relation. The bolt means 17 also has a proximal extremity 27 adapted for connection to the clamping means 21. An elongated chamber 29 extends through the bolt means 17.

The catheter 21 defines therein a lumen 31. The catheter 21 includes a rigid portion 33 adapted to fit slidingly within the opening 29 in the bolt means 17 and a flexible portion 35 adapted to penetrate into a ventricle 37 of the brain, the flexible portion 35 having an opening 39 from the lumen 31 to an exterior surface 41 of the catheter 19 for communication between the lumen 31 and any fluid 43 adjacent the catheter 19.

The clamping means 21 is adapted for connection to the second extremity 27 of the bolt means 17. The clamping means 21 clamps the rigid portion 33 of the catheter 19 in fixed relation to the bolt means 17 whereby the catheter 19 can be inserted through the bolt means 17 into the brain to a desired depth and then clamped to remain in a fixed position with reference to the brain, the clamping means 21 being operative when clamped to forcibly constrain the catheter 19 against movement relative to the bolt means such that a predetermined depth of insertion of the catheter 19 into the brain can be maintained.

The clamping means 21 includes, for example, a threaded cap 45 which screws onto mating threads 47 on the second extremity 27 of the bolt means 17; a collet 49 which encloses the rigid portion 33 of the catheter 19; and an O-ring 51 through which the rigid portion 33 of the catheter 19 passes. The O-ring 51 is located adjacent a solid extremity 53 of the collet 49. A split extremity 55 of the collet 49 is adapted to engage a recess 57 in the cap 45. When the cap 45 is tightened onto the threads 47 of the bolt means 17, the O-ring 51 is compressed between the extremity 53 of the collet 49 and the bolt means 17 and the split extremity 55 of the collet 49 is compressed into the recess 57, tightly clamping the rigid portion 33 of the catheter 19 and forming a sterile connection between the catheter 19 and the bolt means 17.

Thus, the catheter 19 can be slidingly moved back and forth through the opening 29 in the bolt means 17 to position the flexible portion 35 of the catheter 19 in a desired location in the ventricle 37 of the brain and then clamped in position by tightening the cap 45 onto the bolt means 17.

A removable stylet 59 is adapted to fit within the catheter 19 to stiffen the catheter 19 for insertion of the catheter 19 into the brain. After the cap 45 has been tightened, the stylet 59 is removed.

Optionally, a sterility sleeve 61 is adapted to enclose the catheter 19 outside the bolt means 17, the sleeve 61 having a first extremity 63 adapted to define a sterile connection with the clamp means 21, for example by gripping a flange 65 on the cap 45, and a second extremity 67 adapted to define a slidably engaging connection with the catheter 19, for example by a tight friction fit therebetween.

A transducer 69 adapted for insertion into the catheter 19 is operative to provide a signal indicative of ventricular fluid pressure within the brain adjacent the opening 39 in the flexible portion 35 of the catheter 19. A pressure monitor 71 is responsive to the signal to provide a readout of the pressure.

Preferably, means 73 are provided for draining fluid from the brain through the catheter 19; such means 73 include, for example, a vessel 75 to receive the fluid, conduit means 77 to carry the fluid to the vessel 75, and coupling means 79 to couple the conduit means 77 to the catheter 19.

The distal extremity 23 of the bolt means 17 preferably is tapered. The means to define a connection between the bolt means 17 and the skull 15 in a sterile relation comprises the threads 25, the threads 25 being operative when the bolt means 17 is twisted as with a wrench to screw tightly into the opening 13 in the skull 15.

An optional installation kit comprises a drill 81 for drilling an opening through the skull to receive the bolt means 17, a drill stop 83 adapted for installation on the drill 81, means such as an Allen wrench 85 for installing the drill stop 83 at a desired location on the drill 81 to fix a maximum depth to which the drill 81 can penetrate; and means such as a socket wrench 87 for tightening the bolt means 71 into the opening 13, the bolt means 17 having a flattened portion 89 to receive the wrench 87.

In operation, a physician makes an incision through the scalp and uses the drill and drill stop to drill a hole through the skull at a desired location. Then the bolt means 17 is screwed into the hole, forming a connection between the bolt means 17 and the skull in a sterile relation. Next, the stylet 59 is inserted into the catheter 19 and the catheter 19 is inserted through the opening 29 in the bolt means 17 and positioned by the physician in the ventricle 37. Next the cap 45 is tightened, fixing the catheter 19 in position and constraining it against movement relative to the bolt means 17. Finally, the monitor 71 and, if needed, the drain means 73 are connected to the catheter 19 through the coupling 79.

Additional details of the invention are illustrated and described in a preliminary, unreleased brochure attached hereto as Appendix A and incorporated herein by this reference, and in blueprints attached hereto as Appendix B and incorporated herein by this reference.

From the foregoing it will be appreciated that the ventricular catheter of the invention provides a sterile, simple-to-use apparatus for monitoring ventricular pressure in a human brain and for draining fluid to reduce the pressure if needed.

Although certain specific embodiments of the invention have been described and illustrated, the invention is not to be limited to the specific forms or arrangements of parts so described and illustrated, and various modifications and changes can be made without departing from the scope and spirit of the invention. Within the scope of the appended claims, therefore, the invention may be practiced otherwise than as specifically described and illustrated.

We claim:

1. A ventricular catheter assembly for monitoring a brain parameter through an opening in a skull of a living patient, the catheter assembly comprising:
   bolt means having an elongated chamber therethrough, a proximal extremity, and distal extremity adapted for insertion into an opening in the skull in sterile relation;
   a catheter disposed through the chamber in the bolt means, and including a lumen, and a flexible distal extremity for penetrating a ventricle of the brain, the flexible extremity having an opening for the lumen to the exterior of the flexible distal extremity; and
   clamping means connected to the proximal extremity of the bolt means and operative to forcibly engage the catheter and constrain the catheter against movement relative to the bolt means such that a predetermined depth of insertion of the catheter into the brain can be maintained.

2. A catheter assembly according to claim 1 and further comprising a removable stylet adapted to fit within the catheter to stiffen the catheter for insertion of the catheter into the brain.

3. A catheter assembly according to claim 1 and further comprising a sterility sleeve enclosing the catheter and the proximal extremity of the bolt means, the sleeve having a first extremity closely fitted to the proximal extremity of the clamping means, and a second extremity closely fitted to the catheter, thereby enclosing the catheter between the extremities in a sterile relation.

4. A catheter assembly according to claim 1 and further comprising a transducer adapted for insertion into the catheter and operative to provide a signal indicative of ventricular fluid pressure within the brain adjacent the opening in the flexible portion of the catheter.

5. A catheter assembly according to claim 4 and further comprising a pressure monitor responsive to the signal to provide a readout of the pressure.

6. A catheter according to claim 4 and further comprising means for draining fluid from the brain through the catheter.

7. A catheter assembly according to claim 6 wherein the means for draining fluid comprises a vessel to receive the fluid, conduit means to carry the fluid to the vessel, and coupling means to couple the conduit means to the catheter.

8. A catheter assembly according to claim 1 wherein the distal extremity of the bolt means is tapered and comprises male threads on an exterior surface of the distal extremity, the threads being operative when the bolt means is tightened into the opening of the skull to provide the sterile relation.

9. A catheter assembly according to claim 1 including an installation apparatus comprising:
   a drill for drilling an opening through the skull to receive the bolt means;
   a drill stop carried by the drill;
   means fixing the drill stop at a desired location on the drill to establish a maximum depth to which the drill can penetrate; and
   means for tightening the bolt means into the opening.

10. A ventricular catheter assembly for monitoring a brain parameter through an opening in a skull of a living patient, the catheter assembly comprising:
    bolt means having an elongated chamber therethrough, a threaded proximal extremity, and a threaded distal extremity for threading into an opening in the skull in sterile relation;
    a catheter disposed through the chamber in the bolt means and including a lumen and flexible distal extremity for penetrating a ventricle of the brain, the flexible distal extremity being apertured for communication between the lumen and any fluid adjacent the catheter, the catheter defining an annular space with a portion of the walls of the chamber;
    compressible mans disposed in the annular space;
    clamping means threaded onto the proximal extremity of the bolt means and operative to tighten upon the proximal extremity to compress the compressible means against the catheter and constrain the catheter against movement relative to the bolt means such that a predetermined depth of insertion of the catheter into the brain can be maintained.

11. A catheter assembly according to claim 10 and including sealing means in the annular space compressible against the passage of fluids into the chamber from the skull.

12. A catheter assembly according to claim 10 wherein the compressible means comprises a collet.

* * * * *

UNITED STATES PATENT AND TRADEMARK OFFICE
CERTIFICATE OF CORRECTION

PATENT NO. : 4,903,707
DATED : February 27, 1990
INVENTOR(S) : Knute, et al.

It is certified that error appears in the above-identified patent and that said Letters Patent is hereby corrected as shown below:

Column 1, line 51, replace "blot" with --bolt--.

Column 1, line 65, delete "first".

Column 3, line 17, between "means 17" and "the" insert --on--.

Column 3, line 17, replace "fluid-tight" with --sterile--.

Claim 1, Column 5, line 12, delete "for" and insert --from--.

Claim 6, Column 5, line 42, between "catheter" and "according", insert --assembly--.

Claim 8, Column 6, line 7, replace "of" with --in--.

Claim 10, Column 6, line 33, replace "mans" with --means--.

Claim 11, Column 6, line 43, between "ible" and "against" insert --upon operation of the clamping means to seal off the chamber--.

Signed and Sealed this

Seventh Day of July, 1992

*Attest:*

DOUGLAS B. COMER

*Attesting Officer*   Acting Commissioner of Patents and Trademarks